(12) United States Patent
Karch et al.

(10) Patent No.: US 7,268,233 B2
(45) Date of Patent: Sep. 11, 2007

(54) NICKEL-CARBENE, PALLADIUM-CARBENE AND PLATINUM-CARBENE COMPLEXES, THEIR PRODUCTION AND USE IN CATALYTIC REACTIONS

(75) Inventors: Ralf Karch, Kleinostheim (DE); Oliver Briel, Offenbach (DE); Bernd Kayser, Aschaffenburg (DE); Matthias Beller, Ostseebad Nienhagen (DE); Kumaravel Selvakumar, Electronic City B. Lore (IN); Anja Frisch, St. Andrews (GB); Alexander Zapf, Rosenheim (DE)

(73) Assignee: Umicore AG & Co. KG, Hanau (DE)

( * ) Notice: Subject to any disclaimer, the term of this patent is extended or adjusted under 35 U.S.C. 154(b) by 0 days.

(21) Appl. No.: 10/523,894

(22) PCT Filed: Aug. 7, 2003

(86) PCT No.: PCT/EP03/08780

§ 371 (c)(1),
(2), (4) Date: Feb. 27, 2006

(87) PCT Pub. No.: WO2004/014550

PCT Pub. Date: Feb. 19, 2004

(65) Prior Publication Data

US 2006/0122398 A1    Jun. 8, 2006

(30) Foreign Application Priority Data

Aug. 7, 2002  (DE) ................. 102 36 079

Feb. 28, 2003  (DE) ................. 103 08 905

(51) Int. Cl.
*C07F 15/00*  (2006.01)
*B01J 31/00*  (2006.01)

(52) U.S. Cl. .............. 548/101; 502/155; 502/162

(58) Field of Classification Search ............... 548/101; 502/155, 162
See application file for complete search history.

(56) References Cited

U.S. PATENT DOCUMENTS 5,703,269 A    12/1997   Wolfgang et al. ............ 560/19

FOREIGN PATENT DOCUMENTS

DE       100 62 577 A       7/2002

OTHER PUBLICATIONS

International Search Report (EPO), 2003.
McGuinness et al., "Zerovalent Palladium and Nickel Complexes of Heterocyclic Carbenes: Oxidative Addition of Organic Halides, Carbon-Carbon Coupling Processes, and the Heck Reaction", Organometallics, vol. 18, pp. 1596-1605 (1999).

*Primary Examiner*—Porfirio Nazario-Gonzalez
(74) *Attorney, Agent, or Firm*—Kalow & Springut LLP

(57) ABSTRACT

The invention relates to novel monocarbene complexes of nickel, palladium or platinum with electron-deficient olefin ligands, to their preparation and to their use in the homogeneous catalysis of organic reactions.

10 Claims, No Drawings

NICKEL-CARBENE, PALLADIUM-CARBENE AND PLATINUM-CARBENE COMPLEXES, THEIR PRODUCTION AND USE IN CATALYTIC REACTIONS

FIELD OF THE INVENTION

The present invention relates to novel nickel-, palladium- and platinum-carbene complexes, and to their preparation and use in catalytic reactions.

BACKGROUND OF THE INVENTION

More than 80% of the industrially produced chemicals are prepared by catalytic processes. Catalytic processes are generally more economically viable and environmentally friendly than corresponding stoichiometric organic reactions. The homogeneous catalysts used, in addition to acids and bases, are in particular complexes of the noble metals. Nickel, palladium and platinum complexes also find use as homogeneous catalysts in numerous industrial processes and in organic synthesis on the laboratory scale. An important example is the utilization of aryl-X compounds (X=halogen, OTf, $N_2^+$, OMs, C(O)Cl etc.). Especially bromo- and chloroaromatics are versatile intermediates of the chemical industry, for example as precursors for the preparation of agrochemical intermediates, pharmaceuticals, dyes, materials, etc. In addition, nickel and palladium catalysts are frequently employed catalysts for the functionalization of haloaromatics or vinyl halides to aromatic olefins and dienes respectively (Heck reaction, Stille reaction), biaryls (Suzuki reaction, Stille reaction, Kumada reaction, Negishi reaction), alkynes (Sonogashira reaction), carboxylic acid derivatives (Heck carbonylation), amines (Buchwald-Hartwig reaction.

The catalyst systems described for olefinations, alkynylations, carbonylations, arylations, aminations and similar reactions of aryl-X compounds frequently have satisfactory catalytic turnover numbers (TON) only with uneconomic starting materials such as iodoaromatics and activated bromoaromatics. In contrast, in the case of deactivated bromoaromatics and especially in the case of chloroaromatics, generally large amounts of catalyst have to be added in order to attain industrially useful yields (>90%). Owing to the complexity of the reaction mixtures, simple catalyst recycling is additionally not possible, so that even the recycling of the catalyst causes high costs which are generally an obstacle to industrial implementation. In addition, particularly in the case of the preparation of active ingredients or active ingredient precursors, it is undesired to work with large amounts of catalyst, since there is the risk in this case that catalyst residues remain in the product. Relatively recent catalyst systems are based on cyclopalladated phosphines (W. A. Herrmann, C. Broβmer, K. Öfele, C.-P. Reisinger, T. Priermeier, M. Beller, H. Fischer, *Angew. Chem.* 1995, 107, 1989; *Angew. Chem. Int. Ed. Engl.* 1995, 34, 1844) or mixtures of sterically demanding arylphosphines (J. P. Wolfe, S. L. Buchwald, *Angew. Chem.* 1999, 111, 2570; *Angew. Chem. Int. Ed. Engl.* 1999, 38, 2413) or tri-tert-butylphosphine (A. F. Littke, G. C. Fu, *Angew. Chem.* 1998, 110 3586; *Angew. Chem. Int. Ed. Engl.* 1998, 37, 3387) with palladium salts or palladium complexes.

However, inexpensive chloroaromatics cannot always be derivatized in an industrially satisfactory manner by means of the above-described reactions even using such catalysts. The catalyst productivities (expressed as TON) for the reactions mentioned are typically below 10,000, and the turnover frequencies (TOF) below 1,000 $h^{-1}$. Thus, for the achievement of high yields, comparatively high amounts of the expensive catalysts have to be used. In spite of all further developments of the catalysts in recent years, only few industrial implementations of the arylation, carbonylation, olefination, etc., of chloroaromatics have become known to date.

An important example of the industrial use of platinum catalysts is hydrosilylation, for example in the preparation of organosilanes or in the crosslinking of silicone rubber. In such reactions too, the productivity and the reactivity of the catalyst is of course a considerable factor for its industrial employability.

The active palladium catalysts which are commonly used in the context of the activation and further utilization of aryl-X compounds are palladium(0) complexes. The situation is similar for nickel catalysts. Platinum catalysts which are used for the hydrosilylation are platinum(IV), platinum(II) and platinum(0) complexes, of which especially the platinum(0) complexes have high activity and have found widespread use.

SUMMARY OF THE INVENTION

It is an object of the present invention to provide novel nickel, palladium and platinum complexes which can be used directly as catalysts even in reactions on the industrial scale. Owing to their structure, the inventive complexes should afford active and productive catalyst systems which are stable over a very wide temperature and pressure range. The complexes should also be preparable with an acceptable level of complexity and expense from available starting compounds, and present no problems in their handling which might be an obstacle to their use in industrial processes.

DETAILED DESCRIPTION OF THE PREFERED EMBODIMENTS

According to the invention, this object is achieved by novel nickel, palladium and platinum complexes of the formula (I)

$$L^1\text{-M-}L^2 \quad (I)$$

where

M is a nickel, palladium or platinum atom, $L^1$ is a ligand having at least one electron-deficient olefinic double bond and $L^2$ is a monodentate carbene ligand of the formula (II) or (III)

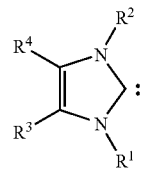
(II)

-continued

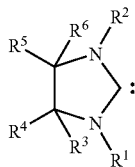

(III)

in which the $R^1$ and $R^2$ radicals are each independently an alkyl radical including a cycloalkyl radical, an aryl radical or heteroaryl radical, each of which may optionally be substituted, and the $R^3$ to $R^6$ radicals are each independently selected from a hydrogen or halogen atom, —$NO_2$, —CN, —COOH, —CHO, —$SO_3H$, —$SO_2$—($C_1$-$C_8$)alkyl, —SO—($C_1$-$C_8$)alkyl, —NH—($C_1$-$C_8$)alkyl, —N(($C_1$-$C_8$)alkyl)$_2$, —NHCO—($C_1$-$C_4$)alkyl, —$CF_3$, —COO—($C_1$-$C_8$)alkyl, —$CONH_2$, —CO—($C_1$-$C_8$)alkyl, —NHCOH, —NH—COO—($C_1$-$C_4$)alkyl, —CO-phenyl, —COO-phenyl, —CH=CH—$CO_2$—($C_1$-$C_8$)alkyl, —CH=$CHCO_2H$, —PO (phenyl)$_2$, —PO(($C_1$-$C_8$)alkyl)$_2$, an optionally substituted alkyl radical, an optionally substituted aryl radical, or an optionally substituted heteroaryl radical, or at least two of the $R^3$ to $R^6$ radicals together with the carbon atoms to which they are bonded form a ring.

Unless specifically stated otherwise, an alkyl radical in the context of the present invention has preferably 1 to 18, more preferably 1 to 12 and most preferably 1 to 8, carbon atoms, for example a methyl, ethyl, iso-propyl, n-propyl, n-butyl, tert-butyl or hexyl group. It may be linear or branched, or form a cyclic structure, in particular a cyclic structure having $C_3$-$C_{18}$, preferably $C_5$-$C_{10}$, for example a cyclohexyl or adamantyl radical. A substituted alkyl radical bears one or more substituents which are preferably each independently selected from —O—($C_1$-$C_8$)alkyl, —O—CO—($C_1$-$C_8$)alkyl, -Ophenyl, -phenyl, a halogen atom, —OH, —$NO_2$, —CN, —COOH, —CHO, —$SO_3H$, —$SO_2$—($C_1$-$C_8$)alkyl, —SO—($C_1$-$C_8$)-alkyl, —$NH_2$, —NH—($C_1$-$C_8$)alkyl, —N(($C_1$-$C_8$)alkyl))$_2$, —NHCO—($C_1$-$C_8$)alkyl, —$CF_3$, —COO—($C_1$-$C_8$)alkyl, —$CONH_2$, —CO—($C_1$-$C_8$)alkyl, —NHCOH, —NHCOO—($C_1$-$C_8$)alkyl$_1$, —CO-phenyl, —COO-phenyl, —CH=CH—$CO_2$—($C_1$-$C_8$)alkyl, —CH=$CHCO_2H$, —PO(phenyl)$_2$ and —PO(($C_1$-$C_8$)alkyl)$_2$.

A substituted alkyl radical may preferably bear up to 8, more preferably 1, 2, 3, 4 or 5, identical or different substituents.

Unless specifically stated otherwise, an aryl radical in the context of the present invention has preferably 6 to 14, more preferably 6 to 10 and most preferably 6, carbon atoms, for example a phenyl, naphthyl or anthryl group. A substituted aryl radical bears one or more substituents which may preferably each independently be selected from —($C_1$-$C_8$) alkyl, —O—($C_1$-$C_8$)alkyl, —OCO—($C_1$-$C_8$)alkyl, —O-phenyl, -phenyl, —($C_6$-$C_{14}$)aryl, a halogen atom, —OH, —$NO_2$, —Si(($C_1$-$C_8$)alkyl)$_3$, —$CF_3$, —CN, —COOH, —CHO, —$SO_3H$, —$NH_2$, —NH—($C_1$-$C_8$)alkyl, —N—(($C_1$-$C_8$)alkyl)$_2$, —P(($C_1$-$C_8$)alkyl)$_2$, —$SO_3$—($C_1$-$C_4$)alkyl, —$SO_2$—($C_1$-$C_6$)alkyl, —SO—($C_1$-$C_6$)-alkyl, —$CF_3$, —NHCO—($C_1$-$C_4$)alkyl, —COO—($C_1$-$C_8$)-alkyl, —$CONH_2$, —CO—($C_1$-$C_8$)alkyl, —NHCOH, —NH-COO—($C_1$-$C_4$)alkyl, —CO-phenyl, —COO-phenyl, —COO—($C_6$-$C_{10}$)aryl, —CO—($C_6$-$C_{10}$)aryl, —CH=CH—$CO_2$—($C_1$-$C_8$)alkyl, —CH=$CHCO_2H$, —P(phenyl)$_2$, —P(($C_1$-$C_8$)alkyl)$_2$, —PO (phenyl)$_2$, —PO(($C_1$-$C_4$)alkyl)$_2$, —$PO_3H_2$ and —PO(O—($C_1$-$C_6$)alkyl)$_2$.

An aryl radical may bear preferably up to 8, more preferably 1, 2, 3, 4 or 5, identical or different substituents.

Unless specifically stated otherwise, a heteroaryl radical in the context of the present invention is preferably a five-, six- or seven-membered ring which, in addition to carbon, has one or more, for example 2 or 3, heteroatoms which are preferably selected from nitrogen, oxygen and/or sulphur atoms, for example a pyrrolidinyl, imidazolidinyl, pyrazolidinyl, piperidyl, tetrahydrofuryl, tetrahydropyryl or piperazinyl group. A substituted heteroaryl radical may have one or more substituents which are each independently selected from —($C_1$-$C_8$)alkyl, —O—($C_1$-$C_8$)alkyl, —OCO—($C_1$-$C_8$)alkyl, —O-phenyl, -phenyl, —($C_6$-$C_{14}$)aryl, a halogen atom, —OH, —$NO_2$, —Si(($C_1$-$C_8$)alkyl)$_3$, —$CF_3$, —CN, —COOH, —CHO, —$SO_3H$, —$NH_2$, —NH—($C_1$-$C_8$)alkyl, —N—(($C_1$-$C_8$)alkyl)$_2$, —P(($C_1$-$C_8$)alkyl)$_2$, —$SO_3$—($C_1$-$C_4$)alkyl, —$SO_2$—($C_1$-$C_6$)alkyl, —SO—($C_1$-$C_6$)alkyl, —$CF_3$, —NHCO—($C_1$-$C_4$)alkyl, —COO—($C_1$-$C_8$)alkyl, —$CONH_2$, —CO—($C_1$-$C_8$)alkyl, —NHCOH, —NH-COO—($C_1$-$C_4$)alkyl, —CO-phenyl, —COO-phenyl, —COO—($C_6$-$C_{10}$)aryl, —CO—($C_6$-$C_{10}$)-aryl, —CH=CH—$CO_2$—($C_1$-$C_8$)alkyl, —CH=$CHCO_2H$, —P(phenyl)$_2$, —P(($C_1$-$C_8$)alkyl)$_2$, —PO(phenyl)$_2$, —PO(($C_1$-$C_4$)alkyl)$_2$, —$PO_3H_2$ and —PO(O—($C_1$-$C_6$)alkyl)$_2$.

A heteroaryl radical may preferably bear 1, 2, 3, 4 or 5 identical or different substituents. Further aromatic, heteroaromatic or/and aliphatic rings may also be fused onto the heteroaryl radical.

The halogen atoms which find use in the context of the present invention are preferably chlorine or fluorine atoms.

Preferred $R^1$ and $R^2$ radicals are an alkyl radical, including a cycloalkyl radical, optionally substituted by one or more substituents selected from —O—($C_1$-$C_8$)alkyl-, —O—CO—($C_1$-$C_8$)alkyl, —Ophenyl, -phenyl, —Cl, —F, —OH, —CN, —COOH, —N(($C_1$-$C_8$)alkyl)$_2$, —$CF_3$, and —COO—($C_1$-$C_8$)alkyl, an aryl radical, optionally substituted by one or more substituents selected from —($C_1$-$C_8$) alkyl, —O—($C_1$-$C_8$)alkyl, —OCO—($C_1$-$C_8$)alkyl, —($C_6$-$C_{14}$)aryl, —Cl, —F, —OH, —$CF_3$, —CN, —COOH, —N(($C_1$-$C_8$)alkyl)$_2$, —COO—($C_1$-$C_8$)alkyl, —P(phenyl)$_2$, and —P(($C_1$-$C_8$)alkyl)$_2$, and a heteroaryl radical, optionally substituted by one or more substituents selected from —($C_1$-$C_8$)alkyl, —O—($C_1$-$C_8$)alkyl, —OCO—($C_1$-$C_8$)alkyl, —($C_6$-$C_{14}$)aryl, —Cl, —F, —OH, —$CF_3$, —CN, —COOH, —N(($C_1$-$C_8$)alkyl)$_2$, —COO—($C_1$-$C_8$)alkyl, —P(phenyl)$_2$, and —P(($C_1$-$C_8$)alkyl)$_2$.

Particularly preferred $R^1$ and $R^2$ radicals are an alkyl radical, including a cycloalkyl radical, optionally substituted by one or more phenyl groups, and an aryl radical optionally substituted by one or more alkyl radicals.

Preferred $R^1$ and $R^2$ radicals are also sterically demanding substituents such as cycloalkyl radicals or aryl radicals, particularly preferred aryl radicals being phenyl radicals which bear one, two or three substituents, for example, in the ortho- and/or para-position. Especially preferred $R^1$ and $R^2$ radicals are 2,4,6-trimethylphenyl, 2,6-dimethylphenyl, 1-adamantyl, tert-butyl, cyclohexyl, O-tolyl, 2,6-diisopropyl-4-methylphenyl and 2,6-diisopropylphenyl groups.

Preferred $R^3$ to $R^6$ radicals are each independently selected from a hydrogen atom, —F, —Cl, —CN, —COOH, —$SO_3H$, —NH—($C_1$-$C_8$)alkyl, —N(($C_1$-$C_8$)alkyl)$_2$, —NHCO—($C_1$-$C_4$)-alkyl, —$CF_3$, —COO—($C_1$-$C_8$)alkyl, —CO—($C_1$-$C_8$)alkyl, —PO-(phenyl)$_2$, —PO(($C_1$-$C_8$)

alkyl)$_2$, an optionally substituted (C$_1$-C$_8$)alkyl radical, an optionally substituted (C$_6$-C$_{14}$)-aryl radical, and an optionally substituted five-, six- or seven-membered heteroaryl radical, or at least two of the R$^3$ to R$^6$ radicals together with the carbon atoms to which they are bonded form a 4-12-membered, preferably a five-, six- or seven-membered, ring. Particularly preferred R$^3$ to R$^6$ radicals are a hydrogen atom and/or an alkyl radical, in particular a methyl or ethyl group. For example, in the case of a particularly preferred embodiment of the carbene ligand of the formula (II), R$^3$ and R$^4$ may be identical and be hydrogen atoms or alkyl radicals. In the case of a particularly preferred embodiment of the carbene ligand of the formula (III), R$^4$ and R$^5$, and R$^3$ and R$^6$, each form identical pairs, each independently selected from hydrogen atoms and alkyl radicals.

In the case of the R$^3$ to R$^6$ radicals, particularly preferred substituents of the alkyl radical are selected from —O—(C$_1$-C$_8$)alkyl, —O—CO—(C$_1$-C$_8$)alkyl, —O-phenyl, -phenyl, —F, —Cl, —OH, —CN, —COOH, —CHO, —SO$_3$H, —NH$_2$, —NH—(C$_1$-C$_8$)alkyl, —N((C$_1$-C$_8$)alkyl)$_2$, NHCO—(C$_1$-C$_4$)-alkyl, —CF$_3$, —COO—(C$_1$-C$_8$)alkyl, —NHCOH, —NHCOO—(C$_1$-C$_4$)-alkyl, —CO-phenyl, —COO-phenyl, —PO(phenyl)$_2$, and —PO—(C$_1$-C$_8$) alkyl)$_2$. Particularly preferred substituents of the aryl radical are selected from —(C$_1$-C$_8$)alkyl, —O—(C$_1$-C$_8$)alkyl, —(C$_6$-C$_{10}$)aryl, —OCO—(C$_1$-C$_8$)alkyl, —O-phenyl, -phenyl, —F, —Cl, —OH, —CF$_3$, —CN, —COOH, —SO$_3$H, —NH$_2$, —NH—(C$_1$-C$_8$)alkyl, —N((C$_1$-C$_8$)alkyl$_2$, —NHCO—(C$_1$-C$_4$)-alkyl, —COO—(C$_1$-C$_8$)alkyl, —CONH$_2$, —CO—(C$_1$-C$_8$)alkyl, —NHCOH, —NH-COO—(C$_1$-C$_4$)alkyl, —CO-phenyl, —COO-phenyl, —COO—(C$_6$-C$_{10}$)aryl, —CO—(C$_6$-C$_{10}$)aryl, —P(phenyl)$_2$, —P((C$_1$-C$_8$)alkyl)$_2$, —PO(phenyl)$_2$, —PO ((C$_1$-C$_4$)alkyl)$_2$, —PO$_3$H$_2$, and —PO(O—(C$_1$-C$_6$)alkyl)$_2$. Particularly preferred substituents of the heteroaryl radical are each independently selected from —(C$_1$-C$_8$)alkyl, —O—(C$_1$-C$_8$)-alkyl, —OCO—(C$_1$-C$_8$)alkyl, —O-phenyl, -phenyl, —F, —Cl, —OH, —CF$_3$, —CN, —COOH, —SO$_3$H, —NH$_2$, —NH—(C$_1$-C$_8$)alkyl, —N((C$_1$-C$_8$) alkyl)$_2$, —NHCO—(C$_1$-C$_4$)alkyl, —COO—(C$_1$-C$_8$)alkyl, —CONH$_2$, —CO—(C$_1$-C$_8$)alkyl, —NHCOH, —NH-COO—(C$_1$-C$_4$)alkyl, —COO—(C$_6$-C$_{10}$)aryl, —CO—(C$_6$-C$_{10}$)aryl, —P(phenyl)$_2$, —P((C$_1$-C$_8$)alkyl)$_2$, —PO (phenyl)$_2$, —PO((C$_1$-C$_4$)alkyl)$_2$, —PO$_3$H$_2$, and —PO(O—(C$_1$-C$_6$)alkyl)$_2$.

Particularly preferred ligands L$^2$ are the following carbenes: 1,3-bis(2,4,6-trimethylphenyl)imidazolinylidene, 1,3-bis(2,6-dimethylphenyl)imidazolinylidene, 1,3-bis(1-adamantyl)-imidazolinylidene, 1,3-bis(tert-butyl)imidazolinylidene, 1,3-bis(cyclohexyl)imidazolinylidene, 1,3-bis(o-tolyl)imidazolinylidene, 1,3-bis(2,6-diisopropyl-4-methylphenyl)imidazolinylidene and 1,3-bis(2,6-diisopropylphenyl)imidazolinylidene, 1,3-bis(2,4,6-trimethylphenyl)4,5-dihydroimidazolinylidene, 1,3-bis-(2,6-dimethylphenyl)-4,5-dihydroimidazolinylidene, 1,3-bis(1-adamantyl)-4,5-dihydroimidazolinylidene, 1,3-bis-tert-butyl)-4,5-dihydroimidazolinylidene, 1,3-bis-(cyclohexyl)-4,5-dihydroimidazolinylidene, 1,3-bis(o-tolyl)-4,5-dihydroimidazolinylidene, 1,3-bis(2,6-diisopropyl-4-methylphenyl)-4,5-dihydroimidazolinylidene and 1,3-bis(2,6-diisopropylphenyl)-4,5-dihydroimidazolinylidene.

The preferred central metal in the inventive complexes is a metal in the 0 oxidation state. Palladium is especially preferred.

Ligands having at least one electron-deficient olefinic double bond L$^1$ are electron-deficient olefins which bear electron-withdrawing substituents on the double bond. Generally suitable for this purpose are substituents whose electronegativity is greater than that of a hydrogen, substituent. Compounds of the formula L$^1$ may have one, two, three or four of these electron-withdrawing substituents on the double bond. Preferred electron-withdrawing substituents are cyano groups or carbonyl radicals, for example aldehyde groups, ketyl radicals, carboxylic acid groups, carboxylic ester radicals, carboxamide radicals, or N-substituted carboxamide radicals.

Compounds of the formula L$^1$ may have one or more, preferably one or two, electron-deficient olefinic double bonds. Particular preference is given to those compounds which do not contain any further olefinic double bonds apart from the electron-deficient olefinic double bond(s).

Special preference is given to compounds which coordinate to the central metal atom by exactly one electron-deficient double bond. These may, for example, be compounds which have exactly one double bond, or else compounds whose structure, for example owing to steric or conformational hindrance, does not allow simultaneous coordination of more than one double bond to the same metal atom. The latter is the case, for example, for quinones which are thus a preferred embodiment of the ligands L$^1$.

Particularly preferred ligands L$^1$ in the context of the present invention are illustrated by the following formulae (IV), (V) and (VI).

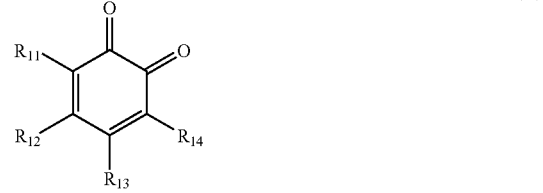

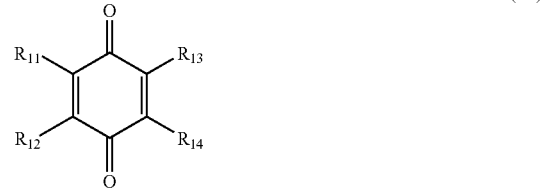

In formula (IV), R$^7$ is selected from —CN, —COH, —COR$^{15}$, —COOH, —COOR$^{15}$, —CONHR$^{15}$, and —CONR$^{15}$R$^{16}$, where R$^{15}$ and R$^{16}$ are each independently a hydrogen atom, a C$_1$-C$_8$ alkyl radical or C$_2$-C$_6$ alkenyl radical, and R$^8$, R$^9$ and R$^{10}$ are each independently selected from a hydrogen atom, a C$_1$-C$_8$ alkyl radical, a C$_2$-C$_8$ alkenyl radical, a halogen atom, a hydroxyl group, —CN, —COH, —COR$^{15}$, —COOH, —COOR$^{15}$, —CONHR$^{15}$ and —CONR$^{15}$R$^{16}$, where R$^{15}$ and R$^{16}$ are each as defined above. Two suitable R$^7$, R$^8$, R$^9$, R$^{10}$, R$^{15}$ and R$^{16}$ radicals may optionally form, for example by condensation of functional groups present therein or replacement of one or more terminal atoms by single or double bonds, together with the atoms to which they are bonded, a 5- to 8-membered, preferably 5- or 6-membered, ring which may preferably be aromatic or partly hydrogenated.

Preferred R[15] and R[16] radicals are selected from a hydrogen atom and an alkyl radical. The alkyl radical has 1 to 8, preferably 1 to 6, more preferably 1 to 4, carbon atoms.

In the formulae (V) and (VI), R[11], R[12], R[13] and R[14] are each independently selected from a hydrogen atom, a $C_1$-$C_8$ alkyl radical, a halogen atom or —CN, or in each case two of the R[11] to R[14] substituents together with the atoms to which they are bonded form a 5- to 8-membered, preferably 5- or 6-membered, ring which may preferably be aromatic or partly hydrogenated.

Preferred R[1], R[12], R[13] and R[14] radicals are hydrogen atoms and alkyl radicals. An alkyl radical has 1 to 8, preferably 1 to 6, more preferably 1 to 4, carbon atoms. Particular preference is given to the case that at least R[11] and R[12] are hydrogen atoms, in which case R[13] and R[14] are likewise hydrogen atoms or alkyl radicals, or form a 6-membered aromatic ring.

Particularly preferred ligands L[1] are acrylic acid, acrylic esters, acrylonitrile, methacrylic acid, methacrylic esters, methacrylonitrile, benzoquinone, 2-methyl-p-benzoquinone, 2,5-dimethyl-p-benzoquinone, 2,3-dichloro-5,6-dicyano-p-benzoquinone, naphthoquinone, anthraquinone, maleic anhydride, maleimide, maleic acid, maleic esters, fumaric acid, fumaric esters, metal salts of the carboxylic acids mentioned, or tetracyanoethene.

In addition to complexes of the formula (I), the present invention also provides dimers of these complexes which are connected via an additional functionality of the ligand L[1]. They have the following structure (Ia) and (Ib):

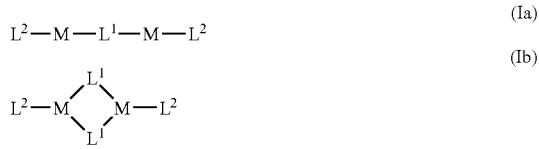

where L[1], L[2] and M are each independently as defined above, with the proviso that the bridging L[1] radical in the formula (Ia) or (Ib) is selected such that it has a further coordination site for an Ni, Pt or Pd atom, for example a carbonyl oxygen or a further electron-deficient olefinic double bond. The dimer of the formula (Ib) appears to form preferentially in crystalline forms, while the complex of the formula (I) is to be found preferentially in solutions.

The invention further provides a process for preparing the novel catalyst complexes by reacting a carbene or a precursor thereof with suitable nickel, palladium or platinum complexes. Suitable complexes are those whose ligands can be displaced readily by carbenes, for example olefin complexes such as Ni(cyclooctadiene)$_2$, Pd$_2$(diallyl ether)$_3$, alkyne or amine complexes (PdMe$_2$(N,N,N',N'-tetramethylethylenediamine)).

Preferred reactants are those complexes which contain (a) a suitable electron-deficient olefin L[1] as a ligand on a nickel, palladium or platinum atom, and (b) a further ligand which can be displaced readily by a carbene. Examples of such ligands which are replaced by the carbene in the synthesis of the complex are cyclooctadiene or norbornadiene, so that the reactant or precursor complex used is, for example, (cyclooctadiene)Pd(benzoquinone) or (norbornadiene)Pd(maleic anhydride). The moiety of the reactant complexes which is composed of the central atom and the ligand with electron-deficient double bond and which is still present in the inventive carbene complex is referred to hereinbelow as the fragment L[1]-M. The precursors of carbenes may, for example, be the imidazolium salts in the presence of bases.

The inventive catalyst may also be prepared in situ from a suitable precursor as described above and the carbene ligand L[2]. To this end, both components are added to the reaction mixture of the reaction to be catalysed. However, such a procedure is not preferred, since the actually active catalyst species first has to be formed here, i.e. the catalyst has to be preformed in order to achieve a maximum activity. Since optimal preformation conditions and optimal reaction conditions for the catalysis reaction are frequently not identical, the catalyst metal is not always optimally utilized. It is therefore advantageous to prepare and to isolate the inventive complexes under controlled conditions and only then to use them as catalysts. In this case, the carbene is preferably reacted with a solution of the reactant complex which contains the fragment L[1]-M at reduced temperature (e.g. at a temperature of −78 to +30° C., preferably at −10° C. to +28° C.). An example of a suitable solvent is THF. The product which forms may be isolated, for example, by concentrating the solution and precipitating. It can additionally be purified by customary processes such as washing, recrystallization or reprecipitation.

According to the invention, the novel complexes are used as catalysts for organic reactions. Typical but nonlimiting examples of such catalytic reactions are olefinations, arylations, alkylations, ketone arylations, aminations, etherifications, thiolizations, silylations, carbonylations, cyanations, alkynylations of aryl-X compounds or vinyl-X compounds, where X is a leaving group, for example a halide, a diazonium salt, triflate, trifluoromethanesulphonate, or olefinic compounds, even in the presence of nucleophiles. Further examples of suitable reactions are hydrosilylations of olefins or alkynes or ketones, carbonylations of olefins, di- and oligomerizations of olefins, telomerizations of dienes, crosscouplings with organometallic reagents (e.g. Grignard reagents, lithium reagents, zinc reagents, tin reagents, etc.) and other transition metal-catalysed coupling reactions. The complexes prepared in accordance with the invention have been found to be especially useful as catalysts for preparing arylated olefins (Heck reactions), biaryls (Suzuki reactions), carboxylic acids and amines from aryl halides or vinyl halides or other aryl-X compounds, for example aryldiazonium salts.

By way of example, the high activity of the inventive complexes is shown in the activation of inexpensive but relatively unreactive chloroaromatics.

In general, the inventive catalyst is used directly without further ligand additions. In this case, stoichiometrically corresponding amounts of L[1], L[2] and M are advantageously used in the preparation of the catalyst. However, it is also possible in catalytic applications to use a preferably small excess of a ligand to the transition metal.

Generally, it is customary to use the inventive catalysts, owing to their activity, in very low transition metal concentrations (<2 mol %). In catalytic applications, preference is given to using transition metal concentrations between 1.5 and 0.0001 mol %, in particular between 1 and 0.01 mol %, of transition metal.

The novel nickel, palladium and platinum complexes are thermally very stable. Thus, the inventive catalysts may be used at reaction temperatures up to above 250° C. Preference is given to using the catalysts at temperatures of −20 to 200° C.; in many cases, it has been found useful to work at temperatures of 30 to 180° C., preferably 40 to 160° C. The complexes may be used without loss of activity even in pressure reactions, for which a pressure of only up to 100 bar is typically used, but preferably in the range of atmospheric pressure up to 60 bar. The stability of the inventive complexes is particularly surprising, since the metal complexes are undercoordinated species.

The catalysts prepared in accordance with the invention may be used, inter alia, for the preparation of aryl-olefins, dienes, biaryls, benzoic acid derivatives, acrylic acid derivatives, arylalkanes, alkynes, amines, ethers, thioethers and silyl compounds. The thus prepared compounds may be used, inter alia, as UV absorbers, as intermediates for pharmaceuticals and agrochemicals, as ligand precursors for metallocene catalysts, as fragrances, active ingredients and monomers for polymers.

EXAMPLES

General Procedure for the Synthesis of the Inventive Complexes:

1 mmol of an Ni, Pd or Pt complex with olefin fragments is suspended in 50 ml of absolute THF. The preparation of suitable reactant complexes is illustrated, for example, in M. Hiramatsu et al., J. Organomet. Chem. 246 (1983) 203, wherein in particular the synthesis of (cyclooctadiene)Pd (quinone) complexes is described. A solution of 1 mmol of carbene in 20 ml of absolute THF is slowly added dropwise at −78° C. The mixture is allowed to warm slowly to room temperature and stirred for a further 2 hours. The solution is concentrated under reduced pressure down to a volume of approx. 2 ml and finally admixed with 25 ml of absolute ether. The precipitated solid is filtered off, washed with ether and dried. The corresponding carbene-metal-olefin complex is obtained in analytically pure form.

With corresponding modification of this method, the following complexes were prepared:

Examples 1 to 14

1

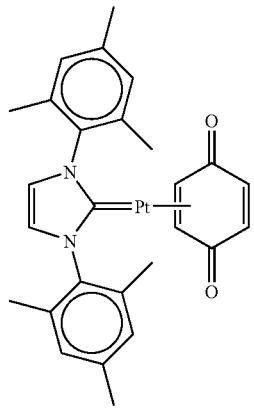

2

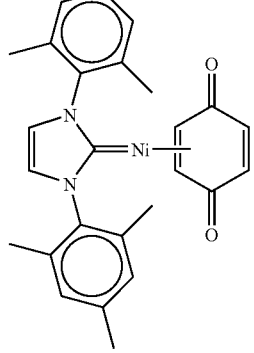

3

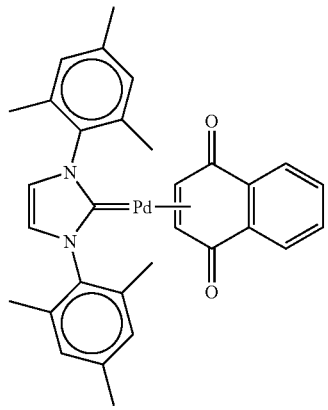

4

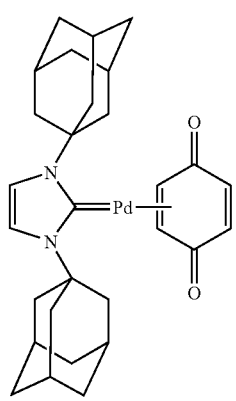

5

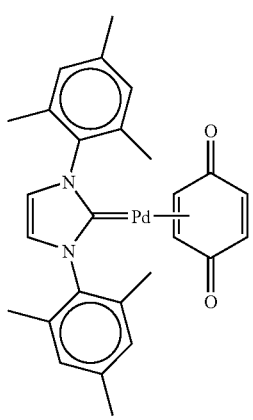

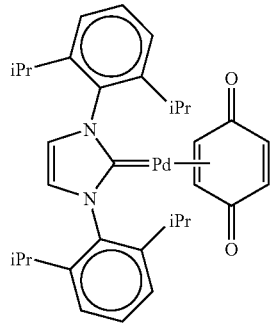
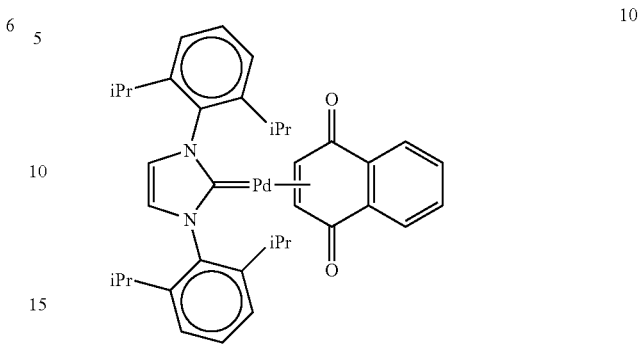
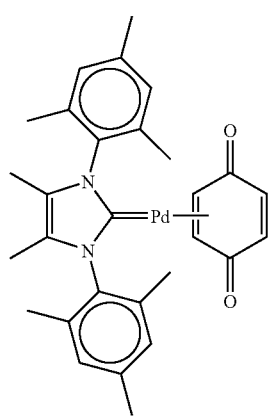
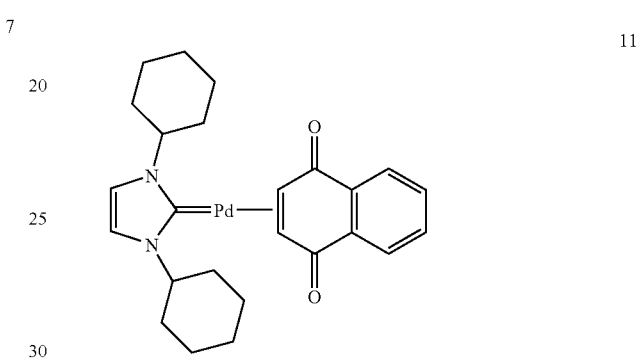
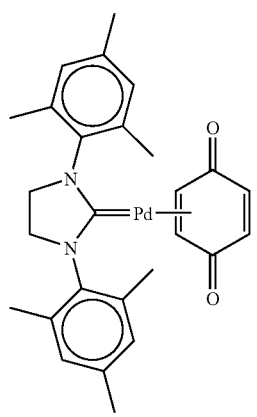
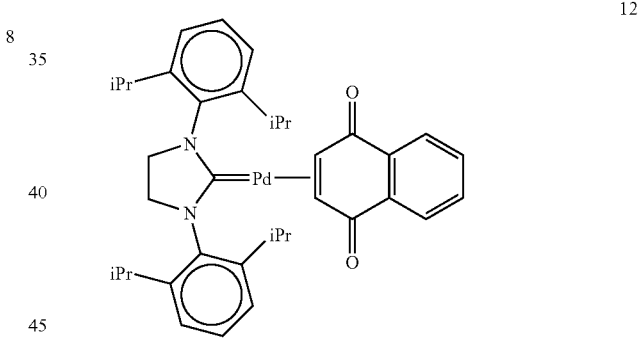
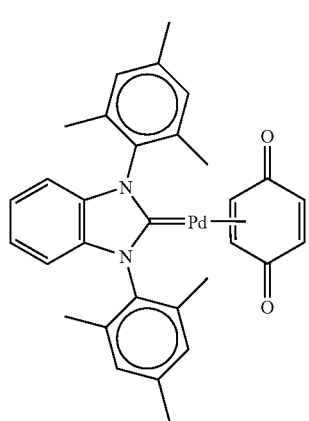
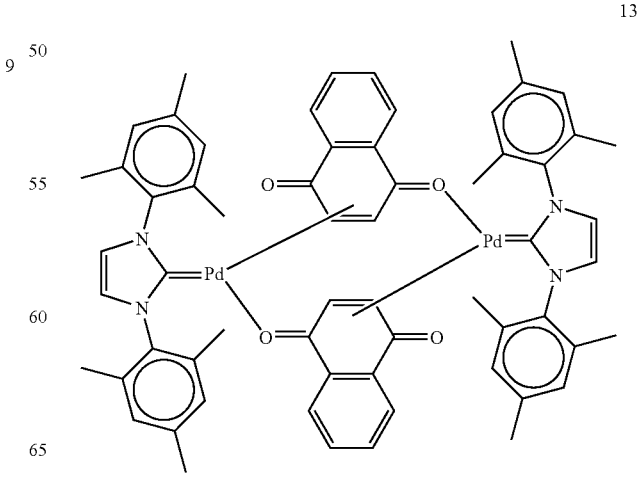

-continued

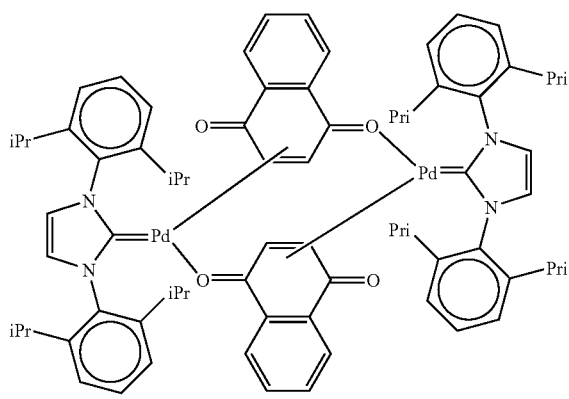

Synthesis of (IMes)Pd(BQ) 1

(BQ)Pd(COD) (323 mg, 1.0 mmol) was suspended in THF (50 ml) under an argon atmosphere and cooled to −78° C. in an acetone-dry ice bath. 1,3-Dimesitylimidazol-2-ylidene (304 mg, 1.0 mmol) dissolved in THF (20 ml) was added slowly with a syringe while stirring. The stirring was continued at −78° C. for 2 h. The acetone-dry ice bath was allowed to warm slowly to room temperature. The dark brown solution was stirred at room temperature for a further 2 h. The solution was filtered (D4 frit) and concentrated to 5 ml by evaporation under reduced pressure. Dried ether (20 ml) was added slowly as a layer. The dark brown fine crystals which had formed were removed and washed with ether and dried under reduced pressure. Yield=440 mg, 85%

Analysis calculated for $C_{27}H_{28}N_2O_2Pd$ (518.95): C, 62.49; H, 5.44; N, 5.39. Found: C, 62.75; H, 5.42; N, 5.30.

Synthesis of (IMes)Pd(NQ) 4

(NQ)Pd(COD) (373 mg, 1.0 mmol) was suspended in THF (50 ml) under an argon atmosphere and cooled to −78° C. in an acetone-dry ice bath. 1,3-Dimesitylimidazol-2-ylidene (304 mg, 1.0 mmol) dissolved in THF (20 ml) was added slowly with a syringe while stirring. A reddish solution formed immediately. The solution was stirred at −78° C. for 2 h. The acetone-dry ice bath was allowed to warm slowly to room temperature. The dark red solution was stirred at room temperature for a further 2 h. The solution was filtered (D4 frit) and concentrated to 5 ml by evaporation under reduced pressure. Dried ether (25 ml) was added slowly as a layer. The red crystals which had formed were removed slowly and washed with ether and dried under reduced pressure. Yield=480 mg, 84%

Analysis calculated for $C_{31}H_{30}N_2O_2Pd$ (569.01): C, 65.44; H, 5.31; N, 4.92. Found: C, 65.79; H, 5.48; N, 4.80.

General Working Method for the Heck Reaction of Aryl Halides:

In a pressure tube (obtainable, for example, from Aldrich), under an argon atmosphere, 1 mmol of aryl halide, 1.5 mmol of olefin, 1.2 mmol of base, a suitable amount of the inventive complex (1 mol %) and 100 mg of diethylene glycol di-n-butyl ether (as an internal standard for the GC analysis) were added to 2 g of an ionic liquid or 5 ml of dioxane. The tube was sealed and suspended in a preheated silicone oil bath. After 24 h, it was allowed to cool to room temperature. The mixture was suspended in ether and the supernatant solution was analysed by gas chromatography.

The products may be isolated by distillation or column chromatography (silica gel, hexane-ethyl acetate mixtures).

Examples 15 to 31

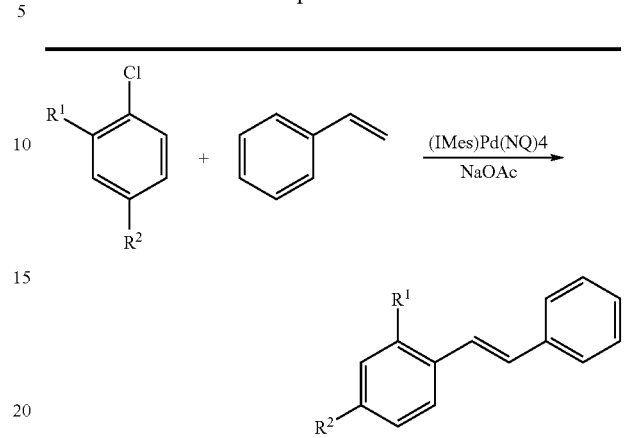

"IMES" means 1,3-bis(2,4,6-trimethylphenyl)imidazolin-ylidene and "NQ" means naphthoquinone.

| No. | $R^1$ | $R^2$ | Sol. | Temp. (° C.) | Conversion (%) | Yield (%) |
|---|---|---|---|---|---|---|
| 15 | H | H | Bu$_4$NBr | 140 | 71 | 62 |
| 16 | H | H | Bu$_4$NBr | 160 | 83 | 67 |
| 17 | H | OCH$_3$ | Bu$_4$NBr | 160 | 63 | 52 |
| 18 | H | NO$_2$ | Bu$_4$NBr | 140 | 100 | 88 |
| 19 | H | Me | Bu$_4$NBr | 160 | 65 | 62 |
| 20 | H | CF$_3$ | Bu$_4$NBr | 140 | 93 | 84 |
| 21 | CN | H | Bu$_4$NBr | 140 | 100 | 99 |
| 22 | 1.1. H | COCH$_3$ | Bu$_4$NBr | 140 | 100 | 97 |
| 23 | 1.2. H | COCH$_3$ | Et$_4$NBr | 140 | 100 | 95 |
| 24 | 1.3. H | COCH$_3$ | dioxane | 140 | 100 | 98 |
| 25 | 1.4. H | CF$_3$ | dioxane | 140 | 95 | 89 |
| 26 | 1.5. H | OCH$_3$ | dioxane | 160 | 65 | 59 |
| 27 | 1.6. F | H | dioxane | 160 | 87 | 82 |

Sol. = solvent

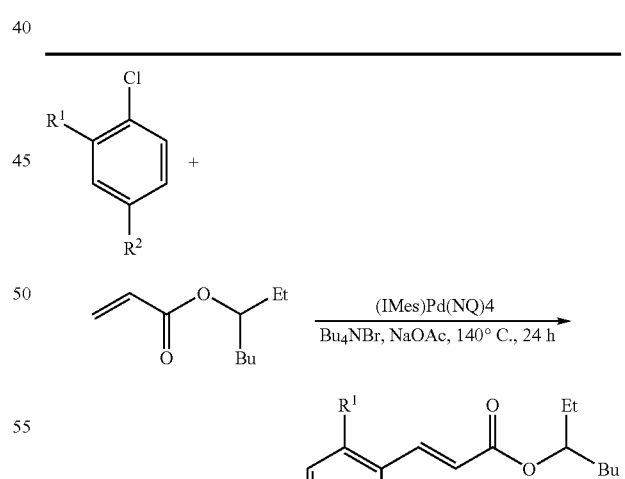

| No. | $R^1$ | $R^2$ | Conversion (%) | Yield (%) |
|---|---|---|---|---|
| 28 | CN | H | 100 | 99 |
| 29 | H | NO$_2$ | 100 | 98 |
| 30 | H | COCH$_3$ | 100 | 99 |
| 31 | H | CF$_3$ | 98 | 90 |

General Working Procedure for the Heck Reaction of Aryldiazonium Salts:

Under an argon atmosphere, 1 mmol of aryldiazonium salt, 1.5 mmol of olefin, a suitable amount of carbene-Pd-olefin catalyst (1 mol %) and 100 mg of diethylene glycol di-n-butyl ether (as an internal standard for the GC analysis) were added to 5 ml of ethanol. The mixture was heated to a suitable temperature for 1 hour and subsequently admixed with ether at room temperature. The solution was analysed by gas chromatography. The products may be isolated by distillation or column chromatography (silica gel, hexane/ethyl acetate mixtures).

Examples 32 to 36

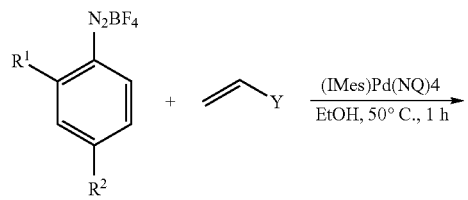

| No. | $R^1$ | $R^2$ | 1.7. Y | Yield (%) |
| --- | --- | --- | --- | --- |
| 32 | H | OMe | Ph | 68 |
| 33 | H | OMe | $CO_2Et$ | 90 |
| 34 | H | OMe | $CO_2CH_2CH(Et)(CH_2)_3CH_3$ | 88 |
| 35 | H | $Net_2$ | $CO_2CH_2CH(Et)(CH_2)_3CH_3$ | 99 |
| 36 | H | $NO_2$ | $CO_2CH_2CH(Et)(CH_2)_3CH_3$ | 96 |

General Working Procedure for the Suzuki Reaction of Aryl Halides

In a pressure tube (obtainable, for example, from Aldrich), under an argon atmosphere, 1 mmol of aryl halide, 1.5 mmol of arylboronic acid, 1.5 mmol of base, a suitable amount of carbene-Pd-olefin catalyst (1 mol %) and 100 mg of diethylene glycol di-n-butyl ether (as an internal standard for the GC analysis) were added to 5 ml of xylene. The tube was sealed and suspended in a preheated silicone oil bath. After 20 h, it was allowed to cool to room temperature. The mixture was suspended in ether, and the supernatant solution was analysed by gas chromatography. The products may be isolated by distillation or column chromatography (silica gel, hexane/ethyl acetate mixtures).

Examples 37 to 43

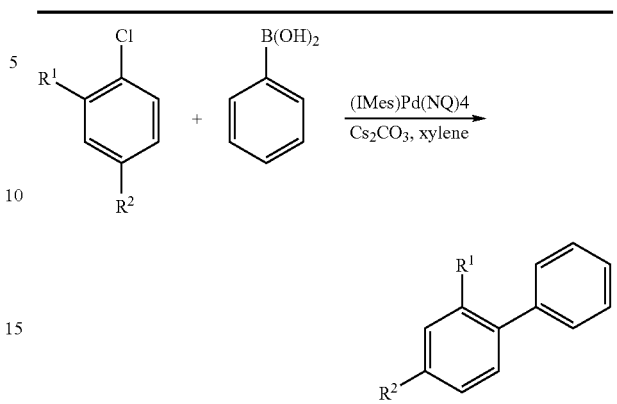

| No. | $R^1$ | $R^2$ | Temp. (° C.) | Conversion (%) | Yield (%) |
| --- | --- | --- | --- | --- | --- |
| 37 | CN | H | 100 | 100 | 98 |
| 38 | H | $NO_2$ | 100 | 100 | 87 |
| 39 | H | $COCH_3$ | 100 | 94 | 88 |
| 40 | H | $CF_3$ | 100 | 89 | 86 |
| 41 | H | H | 120 | 86 | 78 |
| 42 | H | $CH_3$ | 120 | 91 | 84 |
| 43 | H | $OCH_3$ | 120 | 73 | 69 |

General Working Procedure for the Suzuki Reaction of Aryldiazonium Salts:

Under an argon atmosphere, 1 mmol of aryldiazonium salt, 1.2 mmol of arylboronic acid, a suitable amount of carbene-Pd-olefin catalyst (1 mol %) and 100 mg of diethylene glycol di-n-butyl ether (as an internal standard for the GC analysis) were added to 5 ml of ethanol. The mixture was heated to a suitable temperature for 1 hour and subsequently admixed at room temperature with ether. The solution was analysed by gas chromatography. The products may be isolated by distillation or column chromatography (silica gel, hexane/ethyl acetate mixtures).

Examples 44 to 48

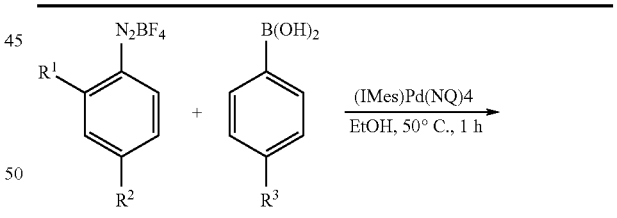

| No. | $R^1$ | $R^2$ | $R^3$ | Yield (%) |
| --- | --- | --- | --- | --- |
| 44 | H | OMe | H | 93 |
| 45 | H | OMe | $CF_3$ | 96 |
| 46 | H | $NEt_2$ | H | 95 |
| 47 | H | $NEt_2$ | $CH_3$ | 89 |
| 48 | H | $NO_2$ | H | 94 |

General Working Procedure for Ketone Arylation:

In a pressure tube (obtainable, for example, from Aldrich), under an argon atmosphere, 1 mmol of aryl halide, 1 mmol of ketone, 1.5 mmol of base, a suitable amount of carbene-Pd-olefin catalyst (1 mol %) and 100 mg of diethylene glycol di-n-butyl ether (as an internal standard for the GC analysis) were added to 5 ml of toluene. The tube was sealed and suspended in a preheated silicone oil bath. After 24 h, it was allowed to cool to room temperature. The mixture was suspended in ether, and the supernatant solution was analysed by gas chromatography. The products may be isolated by distillation or column chromatography (silica gel, hexane/ethyl acetate mixtures).

Examples 49 to 54

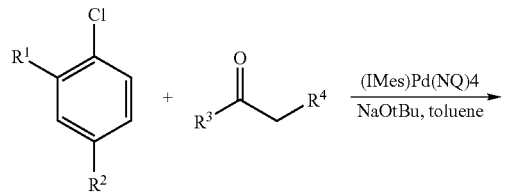

| No. | $R^1$ | $R^2$ | $R^3$ | $R^4$ | Temp. (° C.) | Conversion (%) | Yield (%) |
|---|---|---|---|---|---|---|---|
| 49 | H | H | Ph | H | 120 | 100 | 86 |
| 50 | H | H | Et | Me | 120 | 100 | 91 |
| 51 | H | Me | Ph | Ph | 120 | 87 | 84 |
| 52 | H | OMe | Ph | H | 120 | 73 | 61 |
| 53 | H | $CF_3$ | Ph | Ph | 100 | 95 | 89 |
| 54 | F | H | Et | Me | 100 | 86 | 72 |

General Procedure for the Buchwald-Hartwig Amination:

In a pressure tube (obtainable, for example, from Aldrich), under an argon atmosphere, 1 mmol of aryl halide, 1.2 mmol of amine, 1.4 mmol of base, a suitable amount of carbene-Pd-olefin catalyst (1 mol %) and 100 mg of diethylene glycol di-n-butyl ether (as an internal standard for the GC analysis) were added to 5 ml of toluene. The tube was sealed and suspended in a preheated silicone oil bath. After 24 h, it was allowed to cool to room temperature. The mixture was suspended in ether, and the supernatant solution was analysed by gas chromatography. The products may be isolated by distillation or column chromatography (silica gel, hexane/ethyl acetate mixtures).

Examples 55 to 60

| No. | $R^1$ | $R^2$ | $R^3$ | $R^4$ | Temp. (° C.) | Conversion (%) | Yield (%) |
|---|---|---|---|---|---|---|---|
| 55 | H | COMe | Ph | H | 100 | 93 | 81 |
| 56 | H | H | c-$(CH_2)_5$ |  | 120 | 73 | 69 |
| 57 | H | Me | Ph | Me | 120 | 77 | 74 |
| 58 | H | OMe | mesityl | H | 120 | 64 | 62 |
| 59 | H | $CF_3$ | Bu | Bu | 100 | 84 | 78 |
| 60 | CN | H | Ph | H | 100 | 100 | 89 |

What is claimed is:

1. Transition metal complex of the formula (I)

$$L^1\text{-M-}L^2 \quad (I)$$

where

M is a nickel, palladium or platinum atom, $L^1$ is a ligand having at least one electron-deficient olefinic double bond carrying one, two, three or four substituents, each substituent having an electronegativity greater than that of a hydrogen substituent, and $L^2$ is a monodentate carbene ligand of the formula (II) or (III)

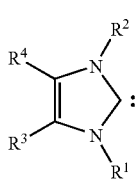

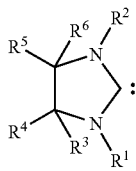

in which the $R^1$ and $R^2$ radicals are each independently an alkyl radical including a cycloalkyl radical, an aryl radical or heteroaryl radical, each of which may optionally be substituted, and the $R^3$ to $R^6$ radicals are each independently selected from a hydrogen or halogen atom, —$NO_2$, —CN, —COOH, —CHO, —$SO_3H$, —$SO_2$—$(C_1$-$C_8)$alkyl, —SO—$(C_1$-$C_8)$alkyl, —NH—$(C_1$-$C_8)$alkyl, —N$((C_1$-$C_8)$alkyl$)_2$, —NHCO—$(C_1$-$C_4)$alkyl, —CF$_3$, —COO—(C$_1$-C$_8$)alkyl, —CONH$_2$, —CO—(C$_1$-C$_8$)alkyl, —NHCOH, —NH—COO—(C$_1$-C$_4$) alkyl, —CO—phenyl, —COO—phenyl, —CH=CH—CO$_2$—(C$_1$-C$_8$)alkyl, —CH=CHCO$_2$H, —PO(phenyl)$_2$, —PO((C$_1$-C$_8$)alkyl)$_2$, an optionally substituted alkyl radical, an optionally substituted aryl radical, or an optionally substituted heteroaryl radical, or at least two of the R$^3$ to R$^6$ radicals together with the carbon atoms to which they are bonded form a 4- to 12-membered ring.

2. Transition metal complex according to claim 1 where M is Pd.

3. Transition metal complex according to claim 1 where the electron-deficient olefinic double bond in L$^1$ bears at least one electron-withdrawing substituent selected from a cyano group, an aldehyde group, a ketyl radical, a carboxylic acid group, a carboxylic ester radical, carboxamide radical or N-substituted carboxamide radical.

4. Transition metal complex according to claim 1 where L$^1$ is selected from compounds of the formulae (IV), (V) or (VI)

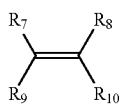

(IV)

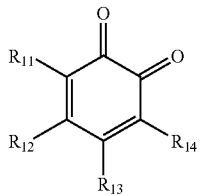

(V)

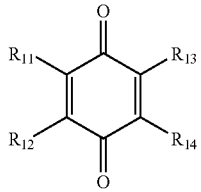

(VI)

in which
R$^7$ is selected from —CN, —COH, —COR$^{15}$, —COOH, —COOR$^{15}$, —CONHR$^{15}$, and —CONR$^{15}$R$^{16}$, where R$^{15}$ and R$^{16}$ are each independently a hydrogen atom, a C$_1$-C$_6$ alkyl radical or C$_2$-C$_6$ alkenyl radical, and
R$^8$, R$^9$ and R$^{10}$ are each independently selected from a hydrogen atom, a C$_1$-C$_8$ alkyl radical, a C$_2$-C$_8$ alkenyl radical, a halogen atom, a hydroxyl group, —CN, —COH, —COR$^{15}$, —COOH, —COOR$^{15}$, —CONHR$^{15}$ and —CONR$^{15}$R$^{16}$, where R$^{15}$ and R$^{16}$ are each as defined above,
or two suitable R$^7$, R$^8$, R$^9$, R$^{10}$, R$^{15}$ and R$^{16}$ radicals together with the atoms to which they are bonded form a 5- to 8-membered ring,
R$^{11}$, R$^{12}$, R$^{13}$ and R$^{14}$ are each independently selected from a hydrogen atom, a C$_1$-C$_8$ alkyl radical, a halogen atom or —CN, or in each case two of the R$^{11}$ to R$^{14}$ substituents together with the atoms to which they are bonded form a 5- to 8-membered ring.

5. Transition metal complex according to claim 1 where L$^1$ is selected from acrylic acid, acrylic esters, acrylonitrile, methacrylic acid, methacrylic esters, methacrylonitrile, benzoquinone, 2-methyl-p-benzoquinone, 2,5-dimethyl-p-benzoquinone, 2,3-dichloro-5,6-dicyano-p-benzoquinone, naphthoquinone, anthraquinone, maleic anhydride, maleimide, maleic acid, maleic esters, fumaric acid, fumaric esters, metal salts of the carboxylic acids mentioned, or tetracyanoethene.

6. Transition metal complex according to claim 1 where L$^2$ is selected from 1,3-bis(2,4,6-trimethylphenyl) imidazolinylidene, 1,3-bis(2,6-dimethylphenyl) imidazolinylidene, 1,3-bis(1-adamantyl)imidazolinylidene, 1,3-bis (tert-butyl) imidazolinylidene, 1,3-bis (cyclohexyl) imidazolinylidene, 1,3-bis(o-tolyl) imidazolinylidene, 1,3-bis(2,6-diisopropyl-4-methylphenyl)imidazolinylidene and 1,3-bis(2,6-diisopropylphenyl) imidazolinylidene, 1,3-bis(2,4,6-trimethylphenyl)-4,5-dihydroimidazolinylidene, 1,3-bis-(2,6-dimethylphenyl)-4,5-dihydroimidazolinylidene, 1,3-bis(1-adamantyl)-4,5-dihydroimidazolinylidene, 1,3-bis (tert-butyl)-4,5-dihydroimidazolinylidene, 1,3-bis-(cyclohexyl)-4,5-dihydroimidazolinylidene, 1,3-bis(o-tolyl)-4,5-dihydroimidazolinylidene, 1,3-bis(2,6-diisopropyl-4-methylphenyl)-4,5-dihydroimidazolinylidene and 1,3-bis(2,6-diisopropylphenyl)-4,5-dihydro-imidazolinylidene.

7. Transition metal complex of the following structure (Ia) or (Ib)

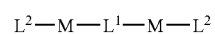

(Ia)

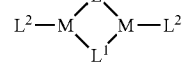

(Ib)

where L$^1$, L$^2$ and M are each independently as defined in claim 1, with the proviso that the bridging L$^1$ radical is selected in such a way that it has a further coordination site for an Ni, Pt or Pd atom.

8. Process for preparing a transition metal complex according to claim 1, comprising the contacting of the ligand L$^2$ with a metal complex which contains the fragment L$^1$-M and an additional ligand which can be displaced readily by the ligand L$^2$, where L$^1$, M and L$^2$ are each as defined in claims 1 to 7.

9. Process for homogenous catalysis of an organic reaction, the process comprising reacting one or more organic reactants in the presence of the transition metal complex according to claim 1 so as to catalyze the organic reaction.

10. Process according to claim 9, wherein the organic reaction is selected from olefinations, arylations, alkylations, ketone arylations, aminations, etherifications, thiolizations, silylations, carbonylations, cyanations or alkynylations of aryl-X compounds or vinyl-X compounds, where X is a leaving group, or of olefinic compounds, or from hydrosilylations of olefins or alkynes or ketones, carbonylations of olefins, di- and oligomerizations of olefins, telomerization of dienes or cross-couplings with organometallic reagents and other transition metal-catalysed coupling reactions.

* * * * *